US007301153B2

(12) United States Patent
Eriksson et al.

(10) Patent No.: US 7,301,153 B2
(45) Date of Patent: Nov. 27, 2007

(54) PHOTO SENSOR PANEL FOR HIGH RESOLUTION PET

(75) Inventors: Lars A. Eriksson, Oak Ridge, TN (US); Matthias J. Schmand, Lenoir City, TN (US); Michael E. Casey, Knoxville, TN (US); Niraj K. Doshi, Knoxville, TN (US); Mehmet Aykac, Knoxville, TN (US); Ronald Nutt, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 79 days.

(21) Appl. No.: 11/387,377

(22) Filed: Mar. 23, 2006

(65) Prior Publication Data

US 2007/0221856 A1 Sep. 27, 2007

(51) Int. Cl.
*G01T 1/20* (2006.01)

(52) U.S. Cl. ............... 250/368; 250/370.1; 250/370.11
(58) Field of Classification Search ................. 250/368
See application file for complete search history.

(56) References Cited

U.S. PATENT DOCUMENTS

2003/0226972 A1* 12/2003 Wong et al. ................. 250/368

* cited by examiner

*Primary Examiner*—David Porta
*Assistant Examiner*—Marcus H Taningco
(74) *Attorney, Agent, or Firm*—Peter L. Kendall

(57) ABSTRACT

Apparatus and method for providing nuclear medical imaging, in particular positron emission tomography, wherein a panel detector including scintillation blocks with a light guide is attached thereto. The scintillation block is arranged to cover a plurality of photosensors in an N by N configuration where there are outer photosensors which share light information from adjacent scintillation blocks and at least one center photosensor which does not share light information from adjacent scintillation blocks.

22 Claims, 4 Drawing Sheets

PHOTO SENSOR PANEL FOR HIGH RESOLUTION PET

BACKGROUND OF THE INVENTION

1. Field of the Invention

The present invention generally relates to positron emission tomography, in particular the arrangement of photomultiplier tubes and scintillation blocks for detection of scintillation events for improved image reconstruction.

2. Description of the Background Art

Nuclear medicine is a unique medical specialty wherein radiation is used to acquire images that show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions that emanate from the body. One or more detectors are used to detect the emitted gamma photons, and the information collected is processed to calculate the position of origin of the emitted photon from the target source. The accumulation of a large number of emitted gamma positions allows an image of the organ or tissue under study to be displayed.

One major technique is Positron Emission Tomography (PET), or coincidence imaging. PET devices are generally based on the "Anger" type camera as disclosed in U.S. Pat. No. 3,011,057. Such cameras are comprised of a scintillation crystal, a light guide and an array of photomultiplier tubes. Radiation interacts with the scintillation crystal, which in turn transforms the energy of absorbed quanta into scintillation light photons. The scintillation light photons spread out from the point of emission. A light guide, generally made up of glass, then directs the light photons to a surface of the photomultiplier tubes (PMTs). The PMTs detect the light and produce an output electronic signal that is proportional to the light energy absorbed. The position of the interaction in the crystal is determined by processing the signals of several PMTs around the site of the emission contact.

In PET, two detectors are positioned on opposite sides of the object of interest, and detect simultaneous pairs of gamma photons emitted from the annihilation of a positron of a high energy radiopharmaceutical. The point of interaction on each detector is calculated and a line is drawn between the two points, thereby forming a line of interaction along which the positron annihilation is considered to have occurred.

A PET system can be designed where a number of panel detectors surround a patient volume in a semi-cylindrical pattern. This pattern could, for example, be hexagonal or octagonal. Coincidences are recorded between the panel detectors in such a way that the activity concentration within the patient volume can be reconstructed providing a 3D volume image.

When a scintillation event occurs, light will be distributed to multiple PMTs around a given locus. The PMT where the scintillation occurs will receive the most light, and therefore produce a signal with greater amplitude. The surrounding PMTs, being further removed from the scintillation event site, will detect less light energy and therefore produce a lesser amplitude signal. The signals, along with the PMTs placement in an x-y coordinate system, are used to calculate the situs of gamma interaction with the camera. The information therein is used to reconstruct the image of the target subject.

Due to the natural physical makeup of the PMTs and the arrangement of the scintillation block, the situs of a scintillation event is determined by such indirect means. Therefore improvements in precisely determining the location of scintillation event lead to improvements in resolution of the resulting image. What is needed therefore is a system or method for arranging the components of a panel such that the position of a scintillation event can be more precisely determined.

SUMMARY OF THE INVENTION

One embodiment of the invention is a panel detector wherein the scintillation blocks and photosensors are arranged to maximize the precision in locating a scintillation event. The scintillation block is a phoswich block having two scintillation layers. A light guide is positioned between the scintillation block and the photosensors such that the light guide can distribute the light received from the scintillation block to the photosensors. The scintillation block is arranged such that it covers a group of photosensors in an N by N configuration, where N is at least 3, and in the preferred embodiment, N is equal to 3. In such a configuration, there are outer photosensors that share light information from adjacent scintillation blocks, as well as at least one center photosensor that does not share information from adjacent scintillation blocks, but instead uniquely identify the particular scintillation block with which it is associated. The outer photosensors are partially covered by adjacent scintillation blocks. There are four corner photosensors that are each covered by the corner of the scintillation block. Because the center photosensors uniquely identify a scintillation block while the outer photosensors share information with adjacent blocks, the position of a scintillation event can be more precisely determined.

DETAILED DESCRIPTION OF THE PREFERRED EMBODIMENTS

Figure 1:
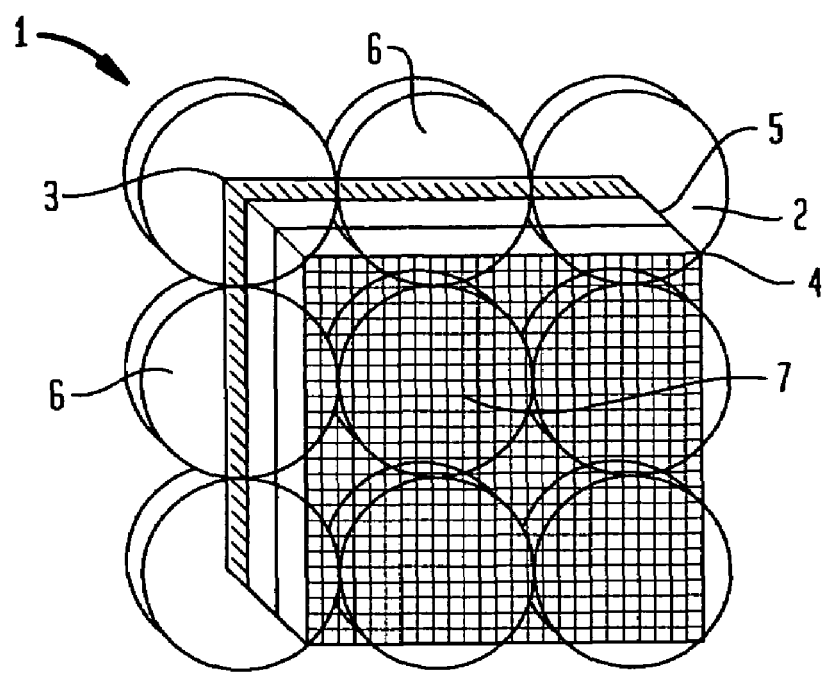
FIG. 1 is perspective view of a scintillation block and its respective photosensors.

One embodiment of the current invention is represented in FIG. 1 wherein a scintillation block and its associated photosensors 1 are displayed. The embodiment consists of a scintillation crystal block 2 fixed to a light guide 3. The light guide 3 can be tunable by means of grooves and/or the thickness of the light guide. The scintillation crystal block is a phoswich block which comprises two scintillators, a lutetium oxyorthosilicate (LSO) scintillator 4 and a Lutetium Yttrium Orthosilicate scintillator (LYSO) 5, or Lutetium Aluminum Perovskite (LuAP) scintillator. Other scintillators already known in the art can make up the phoswich block.

In the preferred embodiment, the scintillation block will be placed over an area of nine photosensors, wherein the photosensors can be, for example, PMTs. The photosensors will be arranged to have a configuration such that there are eight outer photosensors 6 surrounding one central photosensor 7. The outer photosensors 6 are shared with adjacent scintillation blocks and can share light information from adjacent scintillation blocks.

Figure 2A:
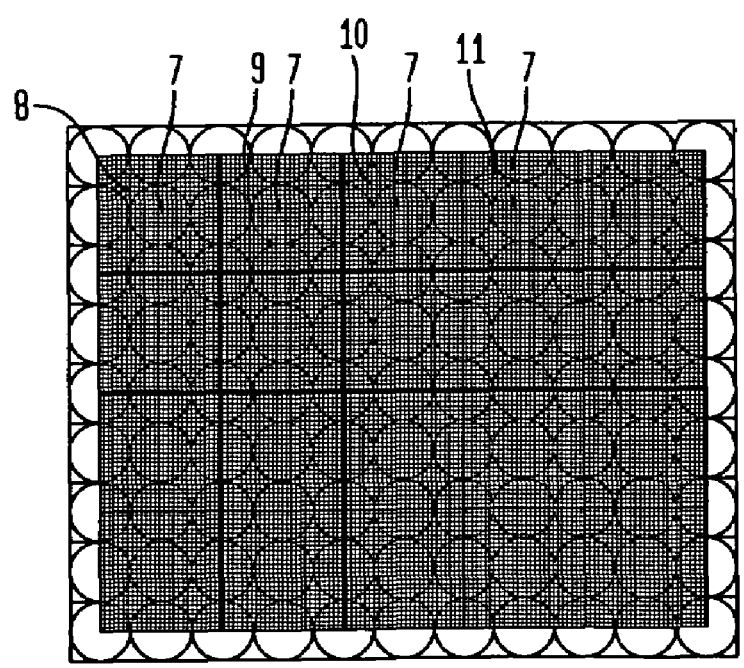
FIG. 2a is a plan view of the preferred embodiment of the panel detector where the scintillation blocks are arranged in a 4 by 5 configuration.

FIG. 2a displays the preferred embodiment of a detector panel with 4 by 5 scintillation blocks. Each scintillation block covers a center photosensor 7. The center photosensor 7 is used for timing and to uniquely identify each scintillation block and the associated photosensors the block covers. For example, scintillation blocks 8, 9, 10, and 11 are all different blocks each identified by a respective central photosensor 7. Furthermore, as shown in FIGS. 1 and 2a, except for the photosensors along the panel edge, the outer photosensors are partially covered by at least one adjacent scintillation block.

In one embodiment of the invention, the scintillation block will have four corners, each covering a photosensor, which is therefore a corner photosensor. The corner photosensors will therefore each be covered or shared by four different scintillation blocks, where the corners of each scintillation block are aligned with the center axis of the photosensor. The outer photosensors that are not covered by a scintillation block corner are covered or shared up to the middle axis of the photosensor by two separate scintillation blocks. The photosensors along the edge of the panel however, may be covered by only one scintillation block. This arrangement can be seen in the preferred embodiment as shown in FIG. 2a.

Figure 2B:
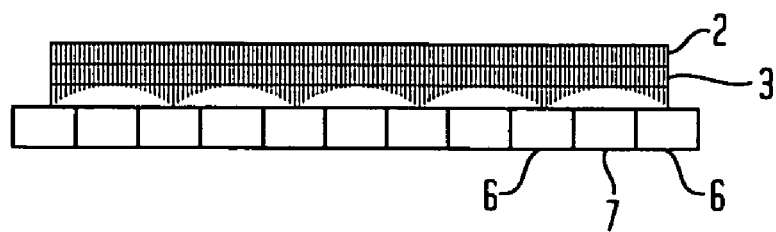
FIG. 2b. is a side view of the preferred embodiment of the scintillation blocks and photosensors with the light guide tuned to optimize the identification of the scintillator elements.

FIG. 2b shows an embodiment wherein the light guide is tuned to optimize the identification of scintillator elements (pixels). In the preferred embodiment, the light guide will attach only to the corner photosensors at their center axis, as shown in FIG. 2b. Furthermore, the panels made up of the multiple shared scintillation blocks can be combined into a polygon with eight or more sides to cover the target patient volume.

Figure 3A:
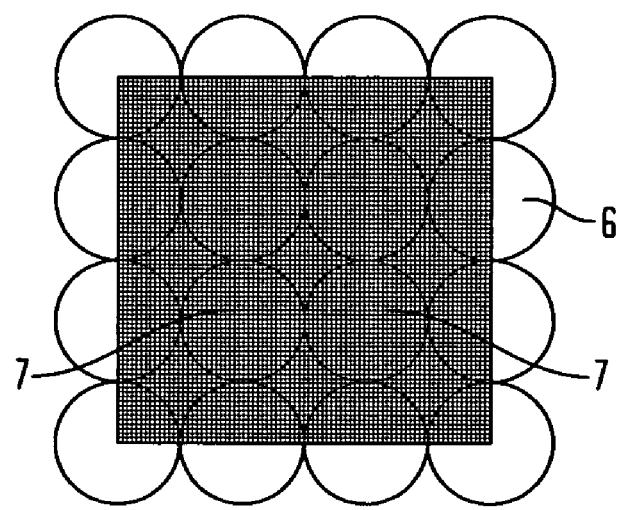
FIG. 3a is a plan view of a scintillation block covering photosensors in a 4 by 4 configuration.
Figure 3B:
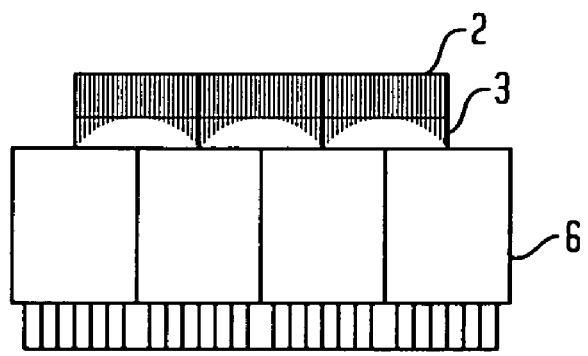
FIG. 3b. is a side view of a scintillation block covering photosensors in a 4 by 4 configuration with the light guide tuned to optimize the identification of the scintillator elements.

The preferred embodiment implements a 3 by 3 configuration as shown in FIG. 1, wherein the scintillation block covers nine photosensors. In other embodiments, the scintillation block can cover a greater number of photosensors. The scintillation block can cover photosensors in an N by N configuration, where N equals 3 in the preferred embodiment, and N may equal 4 or more in other embodiments. Such an alternative embodiment can be seen in FIG. 3a, wherein N equals four. Again, the outer photosensors 6 communicate or share information with adjacent blocks. The center photosensors 7 are used for timing and to uniquely identify the scintillation block. The light guide tuning for identification of scintillator elements is shown in FIG. 3b. In the embodiment in FIG. 3b, the light guide is not attached only to the corner photosensors, but is also to each central axis of each photosensor.

Figure 4A:
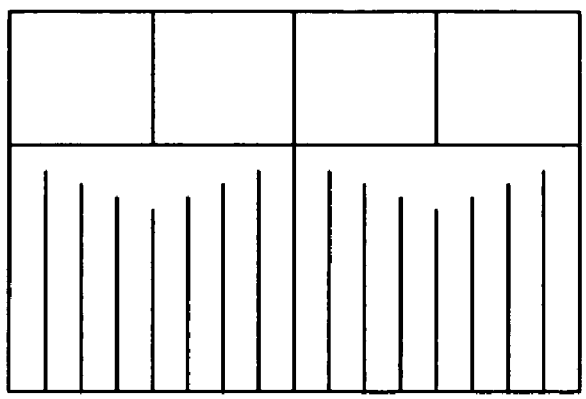
FIG. 4a is a representative side view of an unshared scintillation block configuration where four photosensors are covered by one scintillation block.
Figure 4B:
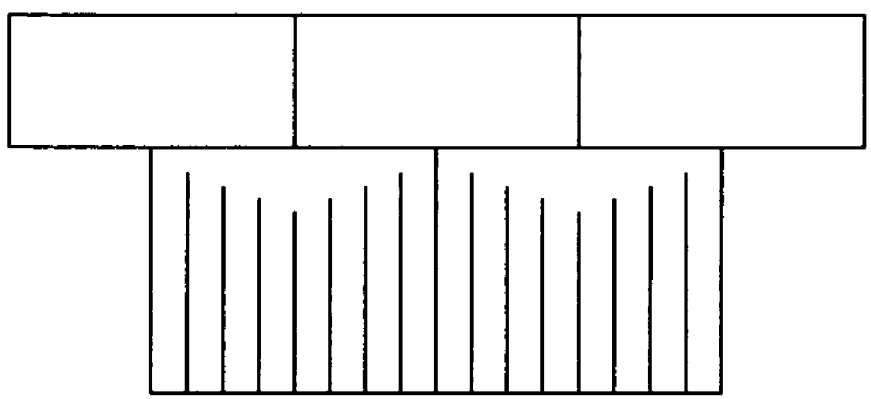
FIG. 4b is a representative side view of a shared scintillation block configuration where four photosensors are covered by one scintillation block.
Figure 4C:
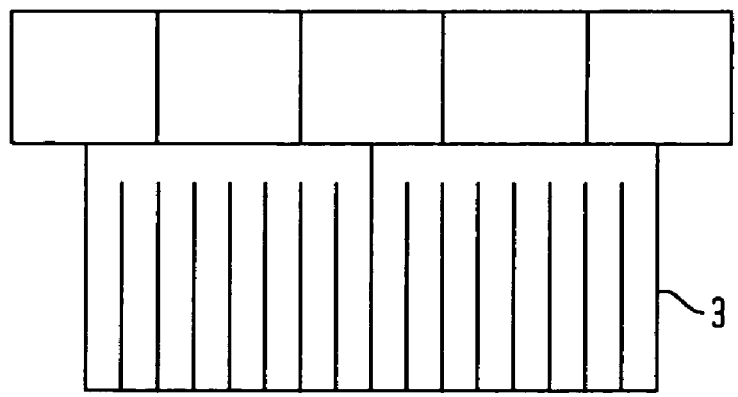
FIG. 4c is a representative side view of the preferred embodiment of the scintillation block and photosensor configuration wherein the outer blocks are shared with adjacent scintillation blocks.

A further configuration of the light guide can be seen in FIG. 4. An unshared configuration of the light guide for scintillation blocks already known in the art can be seen in FIG. 4a, where four photosensors are covered by one scintillation block. As shown, cuts are required for the light guide to give necessary identification information. As displayed in FIG. 4b, four photosensors are again covered by one scintillation block, however, each photosensor is covered by four scintillation block corners. However, in the preferred embodiment of the current invention shown in FIG. 4c, nine photo sensors are covered by one scintillation block, where the outer photosensors share light information from adjacent scintillation blocks. Due to the increased light sampling as a result of the scintillation block's configuration over the photosensors, cuts are no longer required for the light guide.

Figure 5:
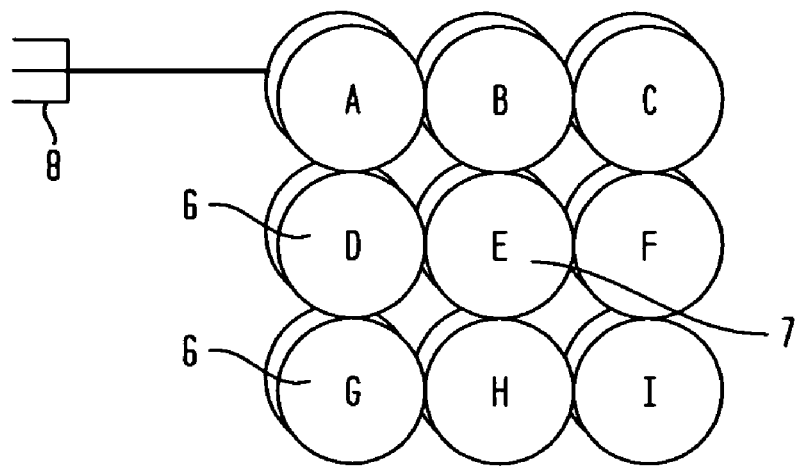
FIG. 5 is a schematic of the preferred embodiment of the photosensor configuration covered by the scintillation block.
Figure 6:
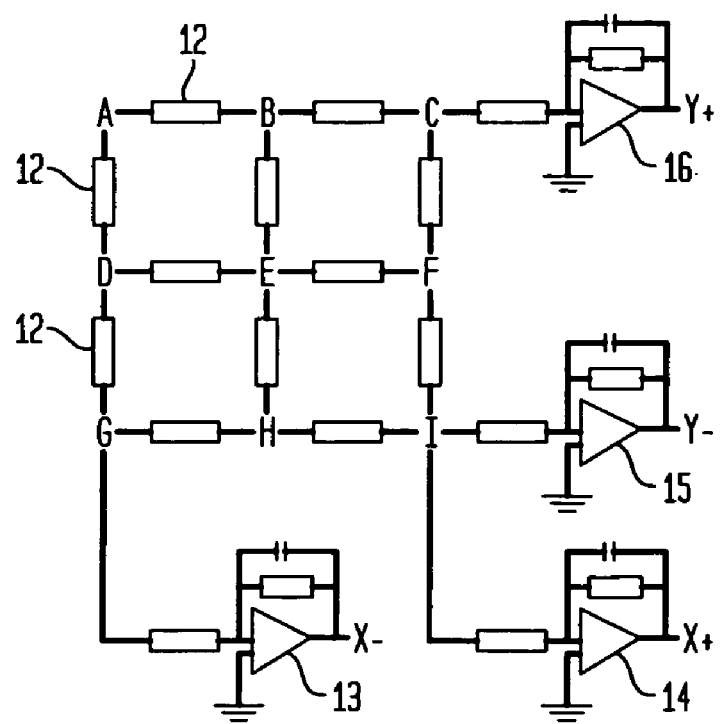
FIG. 6 is a circuit schematic of the preferred embodiment of the photosensor configuration covered by the scintillation block.

In one embodiment, the arrangement of the photomultipliers is displayed in FIG. 5, wherein the signals from the photosensors will be passed to a signal splitter 8. The location of a radiation event on the scintillator is generally determined by sensing the displacement with respect to the X-axis and Y-axis. A schematic of the circuit of one embodiment of the invention can be seen in FIG. 6. Photosensors A, D, and G, are to the left of the central Y axis and so are on the X negative side, whereas, to the right of the Y axis photosensors, C, F, and I are on the X positive side. Furthermore, photosensors A, B, and C are on the Y positive side, and G, H, and I are on the Y negative side. The photosensor signals, depending on where the scintillation occurs and the light received by the individual photosensors, pass through their respective resistors 12, and through the amplifiers 13, 14, 15, and 16 depending on their x, y coordinate position, where 13 is the X-negative amplifier, 14 is the X-positive amplifier, 15 is the Y-negative amplifier and 16 is the Y-positive amplifier. A processor, using the x-y parameters and signal strength then calculates the location of the scintillation event on the scintillator.

Because the center photosensors do not share light information from adjacent scintillation blocks and the outer photosensors do, when a scintillation event occurs on such a scintillation block, the location of the scintillation event can be more precisely determined. For example, if a scintillation event occurs over an outer photosensor, it may not be clear where over the photosensor the event occurred. However, if greater light is received by a center photosensor, then it is likely the event occurred on the scintillation block which is uniquely identified by that center photosensor. Therefore, the position over the outer photosensor where the scintillation event occurred can be more precisely determined. In this way the location of a signal event can be determined with high precision and used to reconstruct a 3D volume image with high resolution.

While illustrative embodiments of the invention have been described herein, the present invention is not limited to the various preferred embodiments described herein, but includes any and all embodiments having equivalent elements, modifications, omissions, combinations (for example, various aspects in different embodiments can be combined together when appropriate in various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited.

What is claimed is:

1. A panel detector for nuclear medical imaging, comprising:
   a plurality of photosensors;
   a first scintillation layer and a second scintillation layer together forming a scintillation block; and
   a light guide positioned such that light received from said scintillation block is distributed to said photosensors, wherein said scintillation block is arranged to cover an N by N configuration of said photosensors, wherein N is at least 3, wherein said configuration of photosensors has outer photosensors that share light information from adjacent scintillation blocks, and wherein said configuration of photosensors has at least one center photosensor that does not share light information from said adjacent scintillation blocks.

2. A panel detector as in claim 1 further comprising a circuit for receiving signals from said photosensors for calculating location of scintillation events wherein an image of a target subject can be reconstructed.

3. A panel detector as in claim 1 wherein N comprises 3.

4. A panel detector as in claim 3 wherein said central photosensor can be used for timing and to uniquely identify one scintillation block.

5. A panel detector as in claim 4 wherein said scintillation block has four corners, and wherein four of said photosensors covered by said scintillation block are each under a corner of said scintillation block, and wherein said light guide is attached only to said corner photosensors.

6. A panel detector as in claim 5 wherein said light guide is tuned to optimize the identification of scintillator elements.

7. A panel detector as in claim 5 wherein adjacent scintillation blocks have four corners, and said corner of said scintillation block and a corner of said adjacent scintillation blocks are aligned with a central axis of said corner photosensors, whereby the photosensor shares information from each scintillation block which it is covered by.

8. A panel detector as in claim 1 wherein said scintillation block covers a portion of said outer photosensors, wherein the remaining portion is covered by at least one adjacent scintillation block.

9. A panel detector as in claim 1 wherein N is equal to four and there are four central photosensors.

10. A panel detector as in claim 1 wherein the photosensors are photomultipliers.

11. A panel detector as in claim 3 wherein said detector panel is arranged such that there are 4 scintillation blocks by 5 scintillation blocks on said panel.

12. A panel detector as in claim 7 wherein said panel detector can be used in cooperation with other panel detectors to obtain images of a target subject.

13. A panel detector as in claim 1 wherein the light guide is without cuts.

14. A panel detector as in claim 1, wherein said nuclear medical images are obtained using Positron Emission Tomography (PET).

15. A panel detector for nuclear medical imaging, comprising:
    a first scintillation layer and a second scintillation layer together forming a scintillation block;
    a light guide attached to said second scintillation layer whereby light received from said scintillation block is distributed;
    a plurality of photosensors covered by said scintillation block in a configuration having outer photosensors and center photosensors wherein outer photosensors are shared with at least one adjacent scintillation block and wherein said center photosensors are not shared with adjacent scintillation blocks.

16. A panel detector as in claim 15 wherein said configuration of photosensors is N by N, wherein N comprises 3.

17. A panel detector as in claim 16 wherein the outer photosensors share light information from said adjacent scintillation blocks.

18. A panel detector as in claim 17 wherein there is only one said central photosensor.

19. A panel detector as in claim 18 wherein said scintillation block has four corners, wherein each corner of said scintillation block covers a photosensor, and wherein the scintillation block is attached only to said photosensors covered by said corner.

20. A panel detector as in claim 15, wherein said nuclear medical images are obtained using Positron Emission Tomography (PET).

21. A positron emission tomography detection method comprising:
    receiving a radiation emission by a scintillation block comprised of two scintillators, wherein a light guide is attached to said scintillation block;
    distributing light from said scintillators through the light guide to photosensors wherein said scintillation block is arranged to cover an N by N configuration of said photosensors, wherein N is at least 3, wherein said configuration of photosensors has outer photosensors that share light information from adjacent scintillation blocks, and wherein said configuration of photosensors has at least one central photosensor that does not share light information from said adjacent scintillation blocks.

22. A panel detector as in claim 21, wherein N comprises 3.

* * * * *